United States Patent
Fujita et al.

(10) Patent No.: US 6,696,598 B2
(45) Date of Patent: Feb. 24, 2004

(54) PROCESS FOR PRODUCING LOWER ALIPHATIC CARBOXYLIC ACID ESTER

(75) Inventors: Ayumu Fujita, Oita (JP); Etsuko Kadowaki, Oita (JP); Meiko Saihata, Oita (JP); Hiroshi Uchida, Oita (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 10/009,900

(22) PCT Filed: Sep. 14, 2001

(86) PCT No.: PCT/JP01/07989
§ 371 (c)(1),
(2), (4) Date: Dec. 14, 2001

(87) PCT Pub. No.: WO02/26691
PCT Pub. Date: Apr. 4, 2002

(65) Prior Publication Data
US 2003/0040641 A1 Feb. 27, 2003

Related U.S. Application Data
(60) Provisional application No. 60/256,911, filed on Dec. 21, 2000.

(30) Foreign Application Priority Data
Sep. 26, 2000 (JP) .......................................... 2000-291350

(51) Int. Cl.$^7$ ............................................... C07C 67/04

(52) U.S. Cl. ....................................................... 560/247
(58) Field of Search ......................................... 560/247

(56) References Cited

U.S. PATENT DOCUMENTS

| | | | |
|---|---|---|---|
| 1,924,615 A | | 8/1933 | Merley et al. |
| 5,861,530 A | * | 1/1999 | Atkins et al. ................ 560/247 |
| 6,187,949 B1 | * | 2/2001 | Froom et al. ................ 560/247 |

FOREIGN PATENT DOCUMENTS

| | | |
|---|---|---|
| EP | 0 757 027 A1 | 2/1997 |
| EP | 0 952 141 A1 | 10/1999 |
| JP | 5186391 | 7/1993 |

* cited by examiner

Primary Examiner—Mark L. Berch
Assistant Examiner—Zachary C. Tucker
(74) Attorney, Agent, or Firm—Sughrue Mion, PLLC

(57) ABSTRACT

A process for producing a lower aliphatic carboxylic acid ester by a gas phase esterification reaction starting from a lower aliphatic carboxylic acid and a lower olefin, comprising adding a lower alcohol corresponding to a hydrate of a lower olefin to the gas phase reaction product, condensing a lower aliphatic carboxylic acid and the lower alcohol and while allowing the conversion into a lower aliphatic carboxylic acid ester to proceed, separating the lower aliphatic carboxylic acid ester. Productivity is increased due to the improvement of the conversion of a lower aliphatic carboxylic acid.

26 Claims, 3 Drawing Sheets

US 6,696,598 B2

PROCESS FOR PRODUCING LOWER ALIPHATIC CARBOXYLIC ACID ESTER

This application is the national stage of PCT/JP01/07989 filed Sep. 14, 2001, and claims benefit pursuant to 33 U.S.C. §119(e)(1) of the filing date of the Provisional Application No. 60/256,911 filed Dec. 21, 2000, pursuant to 35§111(b).

TECHNICAL FIELD

The present invention relates to a process for producing a lower aliphatic carboxylic acid ester, comprising reacting a lower aliphatic carboxylic acid and a lower olefin in a gas phase in the presence of an acid catalyst.

More specifically, the present invention relates to a process for producing a lower aliphatic carboxylic acid ester with high efficiency, where a lower alcohol corresponding to a hydrate of the lower olefin is added to a reaction product containing a lower aliphatic carboxylic acid and a lower aliphatic carboxylic acid ester, obtained by reacting a lower aliphatic carboxylic acid and a lower olefin in a gas phase in the presence of an acid catalyst, to convert the lower aliphatic carboxylic acid in the reaction product into a lower aliphatic carboxylic acid ester and the lower aliphatic carboxylic acid ester is separated and recovered.

BACKGROUND ART

Lower aliphatic carboxylic acid esters are a useful chemical substance for use in various fields such as various industrial materials and solvents. In particular, ethyl acetate is widely used as an alternative organic solvent to the benzene- or toluene-based solvent and various production processes have been proposed therefor and implemented in industry.

The production process of the lower aliphatic carboxylic acid ester, particularly the production process of ethyl acetate can be classified, by taking notice of the starting material therefor, into (1) a method using acetaldehyde, (2) a method using ethanol and acetic acid and (3) a method using ethylene and acetic acid.

Specific examples of the method (1) using acetaldehyde include the method described in Japanese Unexamined Patent Publication No. 11-140016 (JP-A-11-140016). Specific examples of the method (2) using ethanol and acetic acid include the method described in Japanese Unexamined Patent Publication No. 57-130954 (JP-A-57-130954). According to these methods, ethyl acetate can be produced relatively in a high yield but the method (3) using ethylene and acetic acid is recently drawing an attention as a more effective method.

In particular, with respect to the process for producing a lower aliphatic carboxylic acid ester by gas phase esterification starting from a lower aliphatic carboxylic acid and a lower olefin, for example, a production process using a heteropolyacid and/or a salt thereof as a catalyst is disclosed in Japanese Unexamined Patent Publication No. 4-139148 (JP-A-4-139148), No. 4-139149 (JP-A-4-139149), No. 5-65248 (JP-A-5-65248), No. 6-9459 (JP-A-6-9459) and No. 9-118647 (JP-A-9-118647).

In these production processes of a lower aliphatic carboxylic acid ester, the reaction is performed in a gas phase and therefore, the starting lower aliphatic carboxylic acid must be introduced into a reactor in the form of a gas. Accordingly, in view of the effective use of energy necessary for vaporization, it is important to elevate the conversion of the vaporized lower aliphatic carboxylic acid. For this purpose, in the esterification reaction, use of a lower olefin in an amount equivalent to or greater than the lower aliphatic carboxylic acid is generally proposed with an attempt to elevate the conversion of the lower aliphatic carboxylic acid.

In this case, a process described, for example, in Japanese Unexamined Patent Publication No. 5-140036 (JP-A-5-140036) is generally used, where unreacted lower olefin fed in excess is separated from lower aliphatic carboxylic acid ester, lower aliphatic carboxylic acid or the like, using a lower aliphatic carboxylic acid as an absorber liquid and then recycled.

This method, more specifically, the method of using a lower olefin in an amount equivalent to or greater than a lower aliphatic carboxylic acid in the esterification reaction and thereby elevating the conversion of the lower aliphatic carboxylic acid can successfully reduce the energy cost necessary for the vaporization of the lower aliphatic carboxylic acid. However, accompanying the increase in the excess ratio of lower olefin, the recycled amount increases and the energy required therefor increases. That is, the excess ratio of lower olefin has an optimal range in view of the balance between these two starting materials and the proportion where the lower olefin can be used in excess has an upper limit.

Accordingly, only by the above-described method, the improvement in the conversion of lower aliphatic carboxylic acid is limited and in turn, the saving of energy cost necessary for the vaporization of lower aliphatic carboxylic acid is limited.

DISCLOSURE OF THE INVENTION

The object of the present invention is to improve, in the process for producing a lower aliphatic carboxylic acid ester by gas phase esterification reaction starting from a lower aliphatic carboxylic acid and a lower olefin, the conversion of lower aliphatic carboxylic acid, which is difficult to attain only by the method of using a lower olefin in excess to the lower aliphatic carboxylic acid, and thereby provide an efficient production process of a lower aliphatic carboxylic acid ester.

In order to attain the above-described object, the present inventors have made extensive investigations on the process as a whole in the process for producing a lower aliphatic carboxylic acid ester by gas phase esterification reaction starting from a lower aliphatic carboxylic acid and a lower olefin.

As a result, it has been found that when a lower alcohol corresponding to a hydrate of the lower olefin is added to a reaction product during, in the midst of or independently of the process of separating the lower aliphatic carboxylic acid ester from the reaction product containing a lower aliphatic carboxylic acid and a lower aliphatic carboxylic acid ester at the outlet of a reactor where the gas phase esterification reaction of a lower aliphatic carboxylic acid and a lower olefin is performed, and when the lower aliphatic carboxylic acid is condensed with the alcohol to convert into a lower aliphatic carboxylic acid ester and the lower aliphatic carboxylic acid ester is separated, the productivity of lower aliphatic carboxylic acid ester is improved. The present invention has been accomplished based on this finding.

More specifically, the present invention (I) is a process for producing lower aliphatic carboxylic acid ester, comprising reacting a lower aliphatic carboxylic acid and a lower olefin in a gas phase in the presence of an acid catalyst, wherein the production process comprises the following first and second steps:

First step:
a step of adding a lower alcohol corresponding to a hydrate of the lower olefin to the reaction product containing a lower aliphatic carboxylic acid after the gas phase reaction and thereby obtaining a reaction product having added thereto a lower alcohol; and Second step:
a step of condensing the lower aliphatic carboxylic acid and the lower alcohol in the reaction product having added thereto a lower alcohol, obtained in the first step, and while allowing the conversion into a lower aliphatic carboxylic acid ester to proceed, separating the lower aliphatic carboxylic acid ester.

The present invention (II) is a process for producing a lower aliphatic carboxylic acid ester, comprising reacting a lower aliphatic carboxylic acid and a lower olefin in a gas phase in the presence of an acid catalyst, wherein the production process comprises the following first to third steps:

First step:
a step of adding the same lower aliphatic carboxylic acid as used in the above-described reaction to the reaction product containing a lower aliphatic carboxylic acid after the gas phase reaction and thereby obtaining a reaction product having added thereto a lower aliphatic carboxylic acid;

Second step:
a step of adding a lower alcohol corresponding to a hydrate of the lower olefin to the reaction product having added thereto a lower aliphatic carboxylic acid, obtained in the first step, and thereby obtaining a reaction product having added thereto a lower alcohol; and Third step:
a step of condensing the lower aliphatic carboxylic acid and the lower alcohol in the reaction product having added thereto a lower alcohol, obtained in the second step, and while allowing the conversion into a lower aliphatic carboxylic acid ester to proceed, separating the lower aliphatic carboxylic acid ester.

The present invention (III) is a process for producing a lower aliphatic carboxylic acid ester, comprising reacting a lower aliphatic carboxylic acid and a lower olefin in a gas phase in the presence of an acid catalyst, wherein the production process comprises the following first to fourth steps:

First step:
a step of separating the reaction product after the gas phase reaction containing a lower aliphatic carboxylic acid and a lower aliphatic carboxylic acid ester into a moiety substantially containing a lower aliphatic carboxylic acid as the main component and a moiety substantially containing a lower aliphatic carboxylic acid ester as the main component;

Second step:
a step of adding a lower alcohol corresponding to a hydrate of the lower olefin to the moiety substantially containing a lower aliphatic carboxylic acid as the main component, obtained in the first step, and thereby obtaining a product having added thereto a lower alcohol;

Third step:
a step of condensing the lower aliphatic carboxylic acid and the lower alcohol contained in the product having added thereto a lower alcohol, obtained in the second step, to cause conversion into a lower aliphatic carboxylic acid ester; and Fourth step:
a step of separating the lower aliphatic carboxylic acid ester obtained in the third step and thereby obtaining a lower aliphatic carboxylic acid ester.

BRIEF DESCRIPTION OF THE DRAWINGS

The figures each shows a practical embodiment of the present invention (III). In each FIGS., (1) to (4) indicate the place where the first to fourth steps are mainly performed, respectively.

BEST MODE FOR CARRYING OUT THE INVENTION

Figure 1:
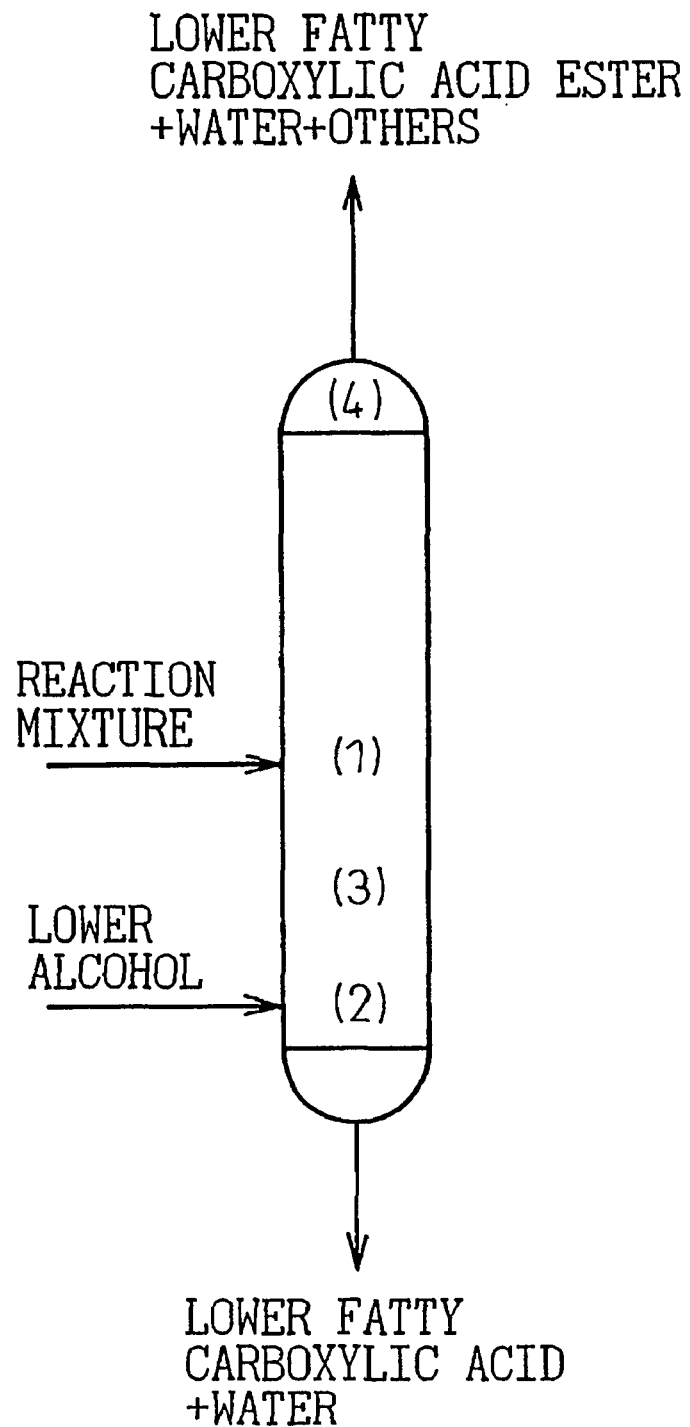
FIG. 1 shows an example of the case where from the first to fourth steps are all performed in a distillation tower as a sole apparatus.

The present invention is described in greater detail below.

The present invention (I) is a process for producing lower aliphatic carboxylic acid ester, comprising reacting a lower aliphatic carboxylic acid and a lower olefin in a gas phase in the presence of an acid catalyst, wherein the production process comprises the following first and second steps:

First step:
a step of adding a lower alcohol corresponding to a hydrate of the lower olefin to the reaction product containing a lower aliphatic carboxylic acid after the gas phase reaction and thereby obtaining a reaction product having added thereto a lower alcohol; and Second step:
a step of condensing the lower aliphatic carboxylic acid and the lower alcohol in the reaction product having added thereto a lower alcohol, obtained in the first step, and while allowing the conversion into a lower aliphatic carboxylic acid ester to proceed, separating the lower aliphatic carboxylic acid ester.

The acid catalyst used in the esterification of a lower aliphatic carboxylic acid and a lower olefin in a gas phase in the present invention (I) is described first. The catalyst is not particularly limited as long as it is an acid catalyst used in general. Preferred examples thereof include heteropolyacids and/or heteropolyacid salts.

The heteropolyacid which is preferred as the acid catalyst for use in the production process of a lower aliphatic carboxylic acid ester of the present invention (I) comprises a center element and peripheral elements to which oxygen is bonded. The center element is usually silicon or phosphorus but the center element is not limited thereto and may be any one element selected from the elements belonging to Groups 1 to 17 of the Periodic Table. The "Periodic Table" as used herein means the Periodic Table according to *Kokusai Junsei Ovobi Oyo Kagaku Rengo Muki Kagaku Meimeiho, Kaitei-Ban (Revised Nomenclature in Inorganic Chemistry by International Pure and Applied Science Association)* (1989).

Specific examples of the center element include cupric ion; divalent beryllium, zinc, cobalt and nickel ions; trivalent boron, aluminum, gallium, iron, cerium, arsenic, antimony, phosphorus, bismuth, chromium and rhodium ions; tetravalent silicon, germanium, tin, titanium, zirconium, vanadium, sulfur, tellurium, manganese, nickel, platinum, thorium, hafnium and cerium ions and other rare earth element ions; pentavalent phosphorus, arsenic, vanadium and antimony ions; hexavalent tellurium ion; and heptavalent iodide ion, however, the present invention is by no means limited thereto.

Specific examples of the peripheral element include tungsten, molybdenum, vanadium, niobium and tantalum, however, the present invention is not limited thereto.

These heteropolyacids are known as "polyoxoanion", "polyoxometallate" or "metal oxide cluster". The structures of some well-known anions are known, for example, as Keggin, Wells-Dawson and Anderson-Evans-Perloff structures. These are described in detail in *Poly-san no Kagaku. Kikan Kagaku Sosetsu (Chemistry of Polyacids, Introduction of Chemistry Quarterly)*, No. 20, edited by Nippon Kagaku Kai (1993). The heteropolyacid usually has a high molecular weight, for example, a molecular weight in the range from 700 to 8,500 and includes not only monomers thereof but also dimeric complexes.

Particularly preferred examples of the heteropolyacid which is preferred as the acid for use in the production process of a lower aliphatic carboxylic acid ester of the present invention (I) include:

tungstosilicic acid
$H_4[SiW_{12}O_{40}] \cdot xH_2O$
tungstophosphoric acid
$H_3[PW_{12}O_{40}] \cdot xH_2O$
molybdophosphoric acid
$H_3[PMo_{12}O_{40}] \cdot xH_2O$
molybdosilicic acid
$H_4[SiMo_{12}O_{40}] \cdot xH_2O$
vanadotungstosilicic acid
$H_{4+n}[SiV_nW_{12-n}O_{40}] \cdot xH_2O$
vanadotungstophosphoric acid
$H_{3+n}[PV_nW_{12-n}O_{40}] \cdot xH_2O$
vanadomolybdophosphoric acid
$H_{3+n}[PV_nMo_{12-n}O_{40}] \cdot xH_2O$
vanadomolybdosilicic acid
$H_{4+n}[SiV_nMo_{12-n}O_{40}] \cdot xH_2O$
molybdotungstosilicic acid
$H_4[SiMo_nW_{12-n}O_{40}] \cdot xH_2O$
molybdotungstophosphoric acid
$H_3[PMo_nW_{12-n}O_{40}] \cdot xH_2O$ wherein n is an integer of 1 to 11 and x is an integer of 1 or more. Of course, the present invention is not limited thereto.

The method for synthesizing these heteropolyacids is not particularly limited and any method may be used. For example, the heteropolyacid can be obtained by heating an acidic aqueous solution (pH: approximately from 1 to 2) containing a salt of molybdic acid or tungstic acid and a simple oxygen acid of hetero atom or a salt thereof. For isolating the heteropolyacid compound from the produced aqueous heteropolyacid solution, a method of crystallizing and separating the compound as a metal salt may be used.

Specific examples thereof are described in *Shin Jikken Kagaku Koza 8, Muki Kagobutsuno Gosei* (III) (*New Experimental Chemistry Course 8, Synthesis* (III) *of Inorganic Compounds*), 3rd ed., edited by Nippon Kagaku Kai, published by Maruzen, page 1413 (Aug. 20, 1984), however, the present invention is not limited thereto. The Keggin structure of the synthesized heteropolyacid can be identified by the X-ray diffraction, UV or IR measurement in addition to the chemical analysis.

The heteropolyacid salt which is preferred as the acid catalyst for use in the production process of a lower aliphatic carboxylic acid ester of the present invention (I) is not particularly limited as long as it is a metal salt or an onium salt resulting from substituting a part or all of the hydrogen atoms of the above-described heteropolyacid.

Specific examples thereof include metal salts such as lithium, sodium, potassium, cesium, magnesium, barium, copper, gold and gallium, and onium salts such as ammonia, of the above-described heteropolyacids, however, the present invention is not limited thereto.

Particularly preferred examples of the heteropolyacid salt include lithium salts, sodium salts, potassium salts, cesium salts, magnesium salts, barium salts, copper salts, gold salts, gallium salts and ammonium salts of the above-described preferred heteropolyacids. Among these, more preferred are lithium salt and cesium salt of tungstosilicic acid, and lithium salt and cesium salt of tungstophosphoric acid.

The heteropolyacid exhibits relatively high solubility in a polar solvent such as water or other oxygen-containing solvents particularly when the heteropolyacid is a free acid or a certain kind of salt, and the solubility can be controlled by appropriately selecting the counter ion.

Examples of the starting material for the element of forming a heteropolyacid salt in the present invention include lithium nitrate, lithium acetate, lithium sulfate, lithium sulfite, lithium carbonate, lithium phosphate, lithium oxalate, lithium nitrite, lithium chloride, lithium citrate, sodium nitrate, sodium acetate, sodium sulfate, sodium carbonate, monosodium phosphate, disodium phosphate, sodium oxalate, sodium nitrite, sodium chloride, sodium citrate, magnesium nitrate hexahydrate, magnesium acetate tetrahydrate, magnesium sulfate, magnesium carbonate, magnesium phosphate tricosahydrate, magnesium oxalate dihydrate, magnesium chloride, magnesium citrate, barium nitrate, barium acetate, barium sulfate, barium carbonate, barium hydrogenphosphate, barium oxalate monohydrate, barium sulfite, barium chloride, barium citrate, copper nitrate, copper acetate, copper sulfate, copper carbonate, copper diphosphate, copper oxalate, copper chloride, copper citrate, aurous chloride, chloroauric acid, auric oxide, auric hydroxide, auric sulfide, aurous sulfide, gallium dichloride, gallium monochloride, gallium citrate, gallium acetate, gallium nitrate, gallium sulfate, gallium phosphate, ammonium acetate, ammonium carbonate, ammonium nitrate, ammonium dihydrogenphosphate, ammonium hydrogencarbonate, ammonium citrate, ammonium nitrate, diammonium phosphate, monoammonium phosphate and ammonium sulfate, however, the present invention is by no means limited thereto.

Among these, preferred are lithium nitrate, lithium acetate, lithium carbonate, lithium oxalate, lithium citrate, sodium nitrate, sodium acetate, sodium carbonate, sodium oxalate, sodium citrate, copper nitrate, copper acetate, copper carbonate, copper citrate, aurous chloride, chloroauric acid, gallium citrate, gallium acetate and gallium nitrate, and more preferred are lithium nitrate, lithium acetate, lithium carbonate, lithium oxalate, lithium citrate, sodium nitrate, sodium acetate, sodium carbonate, sodium oxalate, sodium citrate, copper nitrate, copper acetate, copper carbonate and copper citrate.

Specific examples of the heteropolyacid salt which can be used in the production process of a lower aliphatic carboxylic acid ester of the present invention (I) include lithium salt of tungstosilicic acid, sodium salt of tungstosilicic acid, copper salt of tungstosilicic acid, gold salt of tungstosilicic acid, gallium salt of tungstosilicic acid, lithium salt of tungstophosphoric acid, sodium salt of tungstophosphoric acid, copper salt of tungstophosphoric acid, gold salt of tungstophosphoric acid, gallium salt of tungstophosphoric acid, lithium salt of molybdophosphoric acid, sodium salt of molybdophosphoric acid, copper salt of molybdophosphoric acid, gold salt of molybdophosphoric acid, gallium salt of molybdophosphoric acid, lithium salt of molybdosilicic acid, sodium salt of molybdosilicic acid, copper salt of molybdosilicic acid, gold salt of molybdosilicic acid, gallium salt of molybdosilicic acid, lithium salt of vanadotungstosilicic acid, sodium salt of vanadotungstosilicic acid, copper salt of vanadotungstosilicic acid, gold salt of vanadotungstosilicic acid, gallium salt of vanadotungstosilicic acid, lithium salt of vanadotungstophosphoric acid, sodium salt of vanadotungstophosphoric acid, copper salt of vanadotungstophosphoric acid, gold salt of vanadotungstophosphoric acid, gallium salt of vanadotungstophosphoric acid, lithium salt of vanadomolybdophosphoric acid, sodium salt of vanadomolybdophosphoric acid, copper salt of vanadomolybdophosphoric acid, gold salt of vanadomolybdophosphoric acid, gallium salt of vanadomolybdophosphoric acid, lithium salt of vanadomolybdosilicic acid, sodium salt of vanadomolybdosilicic acid, copper salt of vanadomolybdosilicic acid, gold salt of vanadomolybdo-silicic acid, gallium salt of vanadomolybdosilicic acid, lithium salt of molybdotungstosilicic acid, sodium salt of molybdotungstosilicic acid, copper salt of molybdotungstosilicic acid, gold salt of molybdotungstosilicic acid, gallium salt of molybdotungstosilicic acid, lithium salt of molybdotungstophosphoric acid, sodium salt of molybdo-tungstophosphoric acid, copper salt of molybdotungsto-phosphoric acid, gold salt of molybdotungstophosphoric acid and gallium salt of molybdotungstophosphoric acid.

Among these, preferred are lithium salt of tungstosilicic acid, sodium salt of tungstosilicic acid, copper salt of tungstosilicic acid, gold salt of tungstosilicic acid, gallium salt of tungstosilicic acid, lithium salt of tungstophosphoric acid, sodium salt of tungstophosphoric acid, copper salt of tungstophosphoric acid, gold salt of tungstophosphoric acid, gallium salt of tungstophosphoric acid, lithium salt of molybdophosphoric acid, sodium salt of molybdophosphoric acid, copper salt of molybdophosphoric acid, gold salt of molybdophosphoric acid, gallium salt of molybdophosphoric acid, lithium salt of molybdosilicic acid, sodium salt of molybdosilicic acid, copper salt of molybdosilicic acid, gold salt of molybdosilicic acid, gallium salt of molybdosilicic acid, lithium salt of vanadotungstosilicic acid, sodium salt of vanadotungstosilicic acid, copper salt of vanadotungstosilicic acid, gold salt of vanadotungstosilicic acid, gallium salt of vanadotungstosilicic acid, lithium salt of vanadotungstophosphoric acid, sodium salt of vanadotungstophosphoric acid, copper salt of vanadotungstophosphoric acid, gold salt of vanadotungstophosphoric acid and gallium salt of vanadotungstophosphoric acid.

More preferred are lithium salt of tungstosilicic acid, sodium salt of tungstosilicic acid, copper salt of tungstosilicic acid, gold salt of tungstosilicic acid, gallium salt of tungstosilicic acid, lithium salt of tungstophosphoric acid, sodium salt of tungstophosphoric acid, copper salt of tungstophosphoric acid, gold salt of tungstophosphoric acid, gallium salt of tungstophosphoric acid, lithium salt of vanadotungstosilicic acid, sodium salt of vanadotungstosilicic acid, copper salt of vanadotungstosilicic acid, gold salt of vanadotungsto-silicic acid, gallium salt of vanadotungstosilicic acid, lithium salt of vanadotungstophosphoric acid, sodium salt of vanadotungstophosphoric acid, copper salt of vanadotungstophosphoric acid, gold salt of vanadotungstophosphoric acid and gallium salt of vanadotungstophosphoric acid.

In the acid catalyst for use in the production process of a lower aliphatic carboxylic acid ester of the present invention (I), two or more members selected from the group consisting of the above-described heteropolyacids and/or salts thereof may also be used.

The heteropolyacid and/or the heteropolyacid salt which are preferred as a catalyst for use in esterifying a lower aliphatic carboxylic acid and a lower olefin in the gas phase in the present invention (I) are preferably a so-called supported catalyst where a heteropolyacid and/or a salt thereof as the catalyst component is supported on a support.

The substance which can be used as the support is not particularly limited and a porous substance commonly used as a support may be used. Specific examples thereof include those comprising silica, diatomaceous earth, montmorillonite, titania, activated carbon, alumina or silica alumina, preferably silica, silica alumina or montmorillonite.

The support is also not limited on the shape thereof and may be in the powder, spherical, pellet-like or any other arbitrary state. A sphere or pellet-like state is preferred. The particle size is also not particularly limited and although the preferred particle size varies depending on the reaction form, the average diameter is preferably from 2 to 10 mm in the case of a fixed bed reaction and from powder to 5 mm in the case of a fluidized bed reaction.

The support is most preferably a spherical or pellet-like siliceous support.

The starting lower olefin which can be used in the esterification reaction is an olefin having from 2 to 5 carbon atoms. Specific examples thereof include ethylene, propylene, 1-butene, 2-butene and 1-pentene, with ethylene and propylene being preferred.

The starting lower aliphatic carboxylic acid which can be used is a carboxylic acid having from 1 to 4 carbon atoms. Examples thereof include formic acid, acetic acid, propionic acid, acrylic acid and butyric acid, with acetic acid and acrylic acid being preferred.

In the reaction of the present invention, water is preferably allowed to be present in the starting materials for maintaining the catalytic activity, however, if excess water is present, the selectivity of lower alcohols or ethers corresponding to the starting lower olefin, which are produced as a by-product, increases and this is not preferred. Accordingly, the amount of water allowed to be present in the starting materials has a suitable range. To speak specifically, the amount is preferably from 1 to 10 mol %, more preferably from 2 to 8 mol %.

The reaction form is not particularly limited as long as the reaction is performed in the gas phase and any form may be freely selected from the reaction forms such as fixed bed, moving bed and fluidized bed, by taking account of elimination of heat of reaction, control of reactor, and simplicity and convenience of equipment. In the case where the heat of reaction is small and less affects the control of reaction, an adiabatic reactor, for example, a fixed bed tank-type reactor, is used in many cases because of simplicity and convenience of the equipment. As the reaction heat becomes larger, out of fixed bed reactors, a multi-tubular reactor, a moving bed reactor or a fluidized bed reactor is generally used so as to keep the catalyst layer at a uniform temperature. These are, however, only representative examples and the reaction form is not limited thereto.

The temperature at the reaction is not particularly limited insofar as the medium fed to the reactor is in the gas state, namely, the temperature is higher than the dew point of the mixed gas. The reaction temperature is generally selected in the range from 100 to 250° C., preferably from 120 to 220° C., because in view of the reaction rate, with a low temperature, the reaction rate decreases, whereas as the temperature becomes higher, increase in the reaction rate of the side reaction greatly surpasses the increase in the reaction rate of the main reaction and this causes the reduction of selectivity and adversely affects the reaction results.

With respect to the reaction pressure, since the medium fed to the reactor must be in the gas state, similarly to the temperature, it is important to select a preferred pressure from a temperature-vapor pressure curve showing the relationship of vapor pressure vs. temperature suitable for reaction and temperatures of starting materials, namely, lower olefin and lower aliphatic carboxylic acid, and the temperature of water. In view of the reaction rate, if the pressure lowers, the reaction rate decreases, whereas if the pressure elevates, although the reaction rate increases, the dew point of the mixture of the starting materials lower olefin and lower aliphatic carboxylic acid with water elevates and therefore, the reaction temperature must be set to a high temperature but this causes reduction in the selectivity as described above. Accordingly, the reaction pressure in general is preferably from 0.0 to 3.0 MPaG, more preferably from 0.0 to 2.0 MPaG, though this may vary depending on the kind of the starting materials.

The space velocity (hereinafter simply referred to as "GHSV") of the starting materials fed to the catalytic reactor is not particularly limited, however, if the GHSV is small, the production of lower aliphatic carboxylic acid ester produced within the unit time per the unit volume of catalyst, so-called space time yield (hereinafter simply referred to as "STY") decreases, as a result, the productivity lowers. If the GHSV is increased, the conversion in single passing decreases and unreacted starting materials increase at the reactor outlet. The STY increases nearly in proportion to GHSV at the beginning, however, if the GHSV is excessively increased, the STY does not increase any more and the effect duly expected from the equipment or the operation cost necessary for increasing the GHSV cannot be obtained. In view of this, the GHSV in practice has an optimal range, more specifically, the starting materials are preferably fed to the reaction system at 100 to 7,000/hr, more preferably from 300 to 3,000/hr.

The first step of the present invention (I) is described below. In the first step, the reaction product obtained from the outlet of the reactor where a lower aliphatic carboxylic acid and a lower olefin are reacted in the gas phase in the presence of an acid catalyst is not particularly limited as long as it contains unreacted starting lower aliphatic carboxylic acid. The reaction product may contain, for example, a lower aliphatic carboxylic acid ester, a lower olefin as a starting material, lower alcohols or ethers produced as a by-product upon reaction, or water added for the purpose of maintaining the catalytic activity at the reaction. The reaction product may be the reaction product itself at the gas phase reactor outlet but may also be the reaction product partially separated in advance of performing the first step. For example, those resulting from separating the majority of unreacted lower olefin using an absorption tower or a flash drum may also be used as the reaction product.

In the case of reacting a lower aliphatic carboxylic acid and a lower olefin in a gas phase in the presence of an acid catalyst, the proportion between the starting lower olefin and lower aliphatic carboxylic acid used is in general not particularly limited. However, as described above, the lower olefin is preferably used in an equimolar amount or excess amount to the lower aliphatic carboxylic acid. To speak specifically, the proportion is preferably, in terms of the molar ratio of lower olefin to lower aliphatic monocarboxylic acid, from 1:1 to 30:1 (lower olefin:lower aliphatic monocarboxylic acid), more preferably from 3:1 to 20:1, still more preferably from 5:1 to 15:1.

Even under the above-described condition, the reaction product obtained from the outlet of the reactor where the lower aliphatic carboxylic acid and the lower olefin are reacted in the gas phase contains unreacted lower aliphatic carboxylic acid in many cases and this may be used in the first step of the present invention (I).

The term "a lower alcohol corresponding to a hydrate of the lower olefin" fed in the first step means a hydrate of the lower olefin used in the reaction. Specific examples thereof include ethanol when the lower olefin is ethylene, and include 1-propanol, 2-propanol and/or a mixture thereof when the lower olefin is propylene. The lower alcohol fed in the first step may be a lower alcohol as a by-product in the present invention obtained through separation and recovery or may be a lower alcohol newly fed. A lower alcohol having a higher purity is preferred but this is not particularly limited.

The amount of the lower alcohol added is not particularly limited. From the standpoint of improving the conversion of the objective carboxylic acid, excess feeding of lower alcohol is advantageous, however, if the lower alcohol is fed in excess too much, the energy required in the second step for separating unreacted portion from the lower alcohol fed disadvantageously increases.

Accordingly, the amount added has a preferred range so as to practice the present invention more effectively. Specifically, the amount of lower alcohol in the reaction product having added thereto a lower alcohol is, in terms of the molar ratio to the unreacted lower aliphatic carboxylic acid in the reaction product fed in the first step, preferably from 1:1 to 1:15 (lower alcohol:lower aliphatic carboxylic acid), more preferably from 1:1 to 1:10.

The second step is described below. The second step is a step of converting the lower aliphatic carboxylic acid and the lower alcohol in the reaction product having added thereto a lower alcohol, obtained in the first step, into a lower aliphatic carboxylic acid ester and separating the lower aliphatic carboxylic acid ester from the product.

The reaction product having added thereto a lower alcohol, which is fed to the second step, contains a lower aliphatic carboxylic acid and the lower alcohol added in the first step. In addition, as described above with reference to the first step, the reaction product may further contain a lower aliphatic carboxylic acid ester, a by-product ether, water and a lower alcohol contained as a reaction by-product.

The second step is characterized in that at the time of separating the above-described product, not only a lower aliphatic carboxylic acid ester is simply obtained from the product but also a lower aliphatic carboxylic acid ester is produced by condensing the lower alcohol added and the lower aliphatic carboxylic acid in the reaction product and separated and recovered as the same lower aliphatic carboxylic acid ester as produced by the gas phase reaction between a lower aliphatic carboxylic acid and a lower olefin in the presence of an acid catalyst.

The separation form for use in this process is not particularly limited and a so-called unit operation such as distillation, extraction, absorption and membrane separation may be used. However, in the present invention, a condensation reaction of the lower aliphatic carboxylic acid with the lower alcohol must be performed during the operation and therefore, the pressure and the temperature each has a preferred range. On taking account of the pressure and the temperature satisfying respective preferred ranges and the ease in the separation of a lower aliphatic carboxylic acid ester from the product, distillation operation is preferred.

In the present invention, out of the temperature and the pressure, the temperature having a great effect on the reaction rate is an important factor in the objective esterification reaction between a lower alcohol and a lower aliphatic carboxylic acid. As the temperature is higher, the reaction rate increases. However, since the reaction rate of the side reaction represented by the production of ether as by-product due to dehydration of the lower alcohol also increases and this cause reduction in the yield, the temperature as the operation temperature of separation equipment is preferably from 100 to 200° C., more preferably from 110 to 160° C.

The operation pressure must be decided so as to give a temperature suitable for the reaction but this varies depending on where the separation operation is performed, in a gas phase or in a liquid phase. In the case of a liquid phase, the pressure must be higher than the saturated vapor pressure of the reaction product having added thereto a lower alcohol at the reaction temperature, however, if the pressure is excessively elevated, the equipment costs highly and the merit of the present invention may not be brought out.

On the contrary, in the case of a gas phase, the pressure must be lower than the saturated vapor pressure of the reaction product having added thereto a lower alcohol, however, if the pressure is too low, the objective reaction rate in the gas phase decreases and the effect of the present invention cannot be obtained. Accordingly, whichever gas phase or liquid phase, the operation is preferably performed in the vicinity of saturated vapor pressure of the absorber solution at the operation temperature. To speak specifically, the operation pressure is preferably from 0.0 to 2.0 MPaG, more preferably from 0.0 to 1.0 MPaG.

The first step and the second step of the present invention (I) may be performed using different apparatuses or may be performed in the same apparatus. More specifically, it is possible that the reaction product obtained by reacting a lower aliphatic carboxylic acid and a lower olefin in a gas phase is fed to an apparatus where the first step is performed, a lower alcohol is added thereto, the lower alcohol and the lower aliphatic carboxylic acid are then condensed in a different apparatus and while allowing the conversion into a lower aliphatic carboxylic acid ester to proceed, the lower aliphatic carboxylic acid ester is separated; or that the lower alcohol and the lower aliphatic carboxylic acid are condensed in the apparatus where the first step is performed and while allowing the conversion into a lower aliphatic carboxylic acid ester to proceed, the lower aliphatic carboxylic acid ester is separated.

Specific examples of the method of performing the first and second steps in the same apparatus include a method where a distilling apparatus is used for the apparatus of performing the condensation and separation of the second step, the reaction product obtained by reacting a lower aliphatic carboxylic acid and a lower olefin in a gas phase and a lower alcohol are added to the distilling apparatus, and the first step and the second step are performed without making a clear distinction between the steps or in the order. This method includes such a method that the gas phase reaction product and the lower alcohol are fed to the distilling apparatus through different pipelines and mixed in the distilling apparatus.

In the case where the distilling apparatus is a multistage distillation tower, from the standpoint of efficiently performing the condensation, the position (height) of feeding the gas phase reaction product and the position of feeding the lower alcohol may be differentiated. Specifically, the feeding position of the lower alcohol is preferably lower than the feeding position of the gas phase reaction product. When the feeding positions are differentiated as such, it may be considered that the composition of the gas phase reaction product at the position where the lower alcohol is added differs from the composition at the outlet of the gas phase reaction apparatus, however, needless to say, the present invention (I) includes such a case.

Even in the case of performing the production process of a lower aliphatic carboxylic acid ester of the present invention (I) without making a clear distinction between the first step and the second step using the same apparatus as described above, the preferred conditions of the first step and the second step described above are substantially the same.

The present invention (II) is described below. The present invention (II) is a process for producing a lower aliphatic carboxylic acid ester, comprising reacting a lower aliphatic carboxylic acid and a lower olefin in a gas phase in the presence of an acid catalyst, wherein the production process comprises the following first to third steps:

First step:
  a step of adding the same lower aliphatic carboxylic acid as used in the above-described reaction to the reaction product containing a lower aliphatic carboxylic acid after the gas phase reaction and thereby obtaining a reaction product having added thereto a lower aliphatic carboxylic acid;

Second step:
  a step of adding a lower alcohol corresponding to a hydrate of the lower olefin to the reaction product having added thereto a lower aliphatic carboxylic acid, obtained in the first step, and thereby obtaining a reaction product having added thereto a lower alcohol; and Third step:
  a step of condensing the lower aliphatic carboxylic acid and the lower alcohol in the reaction product having added thereto a lower alcohol, obtained in the second step, and while allowing the conversion into a lower aliphatic carboxylic acid ester to proceed, separating the lower aliphatic carboxylic acid ester.

The first step of the present invention (II) has a purpose of efficiently removing a lower olefin from the reaction product containing the starting lower olefin and lower carboxylic acid and the product lower aliphatic carboxylic acid ester.

It is important that the lower aliphatic carboxylic acid added in the first step is the same as one used in the reaction. This is because the present invention has a purpose of converting unreacted lower aliphatic carboxylic acid in the reaction product into a lower aliphatic carboxylic acid ester by adding thereto a lower alcohol and recovering the lower aliphatic carboxylic acid. If the added carboxylic acid is different from the lower aliphatic carboxylic acid used in the reaction, the objective esterification of the lower aliphatic carboxylic acid may be inhibited or the amount of by-products may disadvantageously increase.

With respect to the amount of the lower aliphatic carboxylic acid used in the first step based on the gas phase reaction product, the operation temperature, the operation pressure and the absorption apparatus used, the method described, for example, in JP-A-5-140036 may be used.

The second step of the present invention (II) is a step of adding a lower alcohol corresponding to a hydrate of the lower olefin used in the reaction to the reaction product having added thereto a lower aliphatic carboxylic acid, obtained in the first step, and thereby obtaining a reaction product having added thereto a lower alcohol. The purpose and means thereof are the same as those of the first step in the present invention (I).

Accordingly, the kind of the lower alcohol added in the second step and the amount thereof based on the lower aliphatic carboxylic acid absorber solution may be the same as those in the first step of the present invention (I).

The third step of the present invention (II) is a step of condensing the lower aliphatic carboxylic acid and the lower alcohol in the reaction product having added thereto a lower alcohol, obtained in the second step, and while allowing the conversion into a lower aliphatic carboxylic acid ester to proceed, separating the lower aliphatic carboxylic acid ester. This step may be performed in the same manner as the second step of the present invention (I). That is, with respect to the embodiment including form of separation apparatus, operation temperature and operation pressure, the same embodiment as in the second step of the present invention (I) may be used.

Also in the present invention (II), similarly to the present invention (I), the step of adding a lower alcohol to obtain a reaction product having added thereto a lower alcohol and the step of condensing the lower aliphatic carboxylic acid and the lower alcohol and while allowing the conversion into a lower aliphatic carboxylic acid ester to proceed, separating the lower aliphatic carboxylic acid ester are preferably performed by distillation and separation.

Furthermore, similarly to the present invention (I), the separation by distillation is preferably performed without making a distinction between the second step and the third step. That is, by performing the second step and the third step of the present invention (II) in the same apparatus, the lower aliphatic carboxylic acid ester can be more efficiently obtained. In the case of performing the second step and the third step without making a distinction therebetween, the embodiment including temperature, pressure and starting material-feeding position is the same as in the present invention (I).

The present invention (III) is described below. The present invention (III) is a process for producing a lower aliphatic carboxylic acid ester, comprising reacting a lower aliphatic carboxylic acid and a lower olefin in the gas phase in the presence of an acid catalyst, wherein the production process comprises the following first to fourth steps:

First step:
a step of separating the reaction product after the gas phase reaction containing a lower aliphatic carboxylic acid and a lower aliphatic carboxylic acid ester into a moiety substantially containing a lower aliphatic carboxylic acid as the main component and a moiety substantially containing a lower aliphatic carboxylic acid ester as the main component;

Second step:
a step of adding a lower alcohol corresponding to a hydrate of the lower olefin to the moiety substantially containing a lower aliphatic carboxylic acid as the main component, obtained in the first step, and thereby obtaining a product having added thereto a lower alcohol;

Third step:
a step of condensing the lower aliphatic carboxylic acid and the lower alcohol contained in the product having added thereto a lower alcohol, obtained in the second step, to cause conversion into a lower aliphatic carboxylic acid ester; and Fourth step:
a step of separating the lower aliphatic carboxylic acid ester obtained in the third step and thereby obtaining a lower aliphatic carboxylic acid ester.

The first step of the present invention (III) is a step of separating the reaction product containing a lower aliphatic carboxylic acid and a lower aliphatic carboxylic acid ester after the gas phase reaction into a moiety substantially containing a lower aliphatic carboxylic acid as the main component and a moiety substantially containing a lower aliphatic carboxylic acid as the main component.

The terms "a moiety substantially containing a lower aliphatic carboxylic acid as the main component" and "a moiety substantially containing a lower aliphatic carboxylic acid ester as the main component" as used herein mean that when the reaction product obtained after the gas phase reaction is divided into two or more moieties, the moiety increased in the lower aliphatic carboxylic acid content than the contents of lower aliphatic carboxylic acid and lower aliphatic carboxylic acid ester in the original reaction product is called "a moiety substantially containing a lower aliphatic carboxylic acid as the main component" and the moiety increased in the lower aliphatic carboxylic acid ester content is called "a moiety substantially containing a lower aliphatic carboxylic acid ester as the main component".

Accordingly, needless to say, these include the case of obtaining, depending on the separation method and the separation conditions, a moiety failing in the complete separation between the lower aliphatic carboxylic acid and the lower aliphatic carboxylic acid ester and allowing partial mixing of respective components or a moiety containing lower alcohols or ethers as by-products generated in the gas phase reaction and additionally containing the added water. This third moiety mainly containing by-products, water or the like may of course be separated independently of the "moiety substantially containing a lower aliphatic carboxylic acid as the main component" or the "moiety substantially containing a lower aliphatic carboxylic acid ester as the main component".

Specific examples of the first step include a method of performing the separation using a distilling apparatus and this method is preferred. In the case where the gas phase reaction product is separated into "a moiety substantially containing a lower aliphatic carboxylic acid as the main component" and "a moiety substantially containing a lower aliphatic carboxylic acid ester as the main component" using a distillation tower as the distilling apparatus, the "moiety substantially containing a lower aliphatic carboxylic acid ester as the main component" can be obtained from the top of the distillation tower and the "moiety substantially containing a lower aliphatic carboxylic acid as the main component" can be obtained from the bottom because the boiling point of the lower aliphatic carboxylic acid is generally higher than the boiling point of the lower aliphatic carboxylic acid ester.

At this time, the by-products lower alcohol or ethers or the added water and the like are shared to any of the moieties depending on the composition of the gas phase reaction product, the performance of the distillation tower and the conditions such as temperature and pressure. Of course, it is preferred to obtain the lower aliphatic carboxylic acid and/or the lower aliphatic carboxylic acid ester to a high purity as much as possible by using a high-performance distilling apparatus or combining a plurality of distillation towers, however, this is not an essential requirement.

One of the purposes of the first step is to facilitate the mixture of the lower aliphatic carboxylic acid and the lower alcohol to shift the equilibrium toward the lower aliphatic carboxylic acid ester side as much as possible at the third step following the subsequent second step. The conditions therefor can be freely selected insofar as this purpose can be attained and the precision in the separation of the first step is not limited. In order to perform the third step of condensing the lower aliphatic carboxylic acid and the lower alcohol with good efficiency, a lower aliphatic carboxylic acid ester is preferably excluded as much as possible from the obtained "moiety substantially containing a lower aliphatic carboxylic acid as the main component".

The subsequent second step is a step of adding a lower alcohol to the "moiety substantially containing a lower aliphatic carboxylic acid as the main component" obtained in the first step. Specifically, the step is the same as the first step of the present invention (I) or the second step of the present invention (II).

As described later, in one specific example of the present invention (III), the first step of separating the gas phase reaction product into "a moiety substantially containing a lower aliphatic carboxylic acid as the main component" and "a moiety substantially containing a lower aliphatic carboxylic acid ester as the main component" and the second step of adding a lower alcohol are performed using the same apparatus, particularly in a distillation tower as one distilling apparatus, and in this case, the positions of feeding the gas phase reaction product and feeding the lower alcohol to the distillation tower are not particularly limited. The position of feeding the lower alcohol is preferably lower than the position of feeding the gas phase reaction product. The most preferred positions vary depending on the performance of the distillation tower, the conditions in the separation, the feeding rate of the gas phase reaction product and the like. In general, the above-described positional relationship is preferred so as to enhance the efficiency in the third step of condensing the lower aliphatic carboxylic acid and the lower alcohol.

The details of the third step and the fourth step are the same as the second step of the present invention (I) or the third step of the present invention (II).

Figure 2:
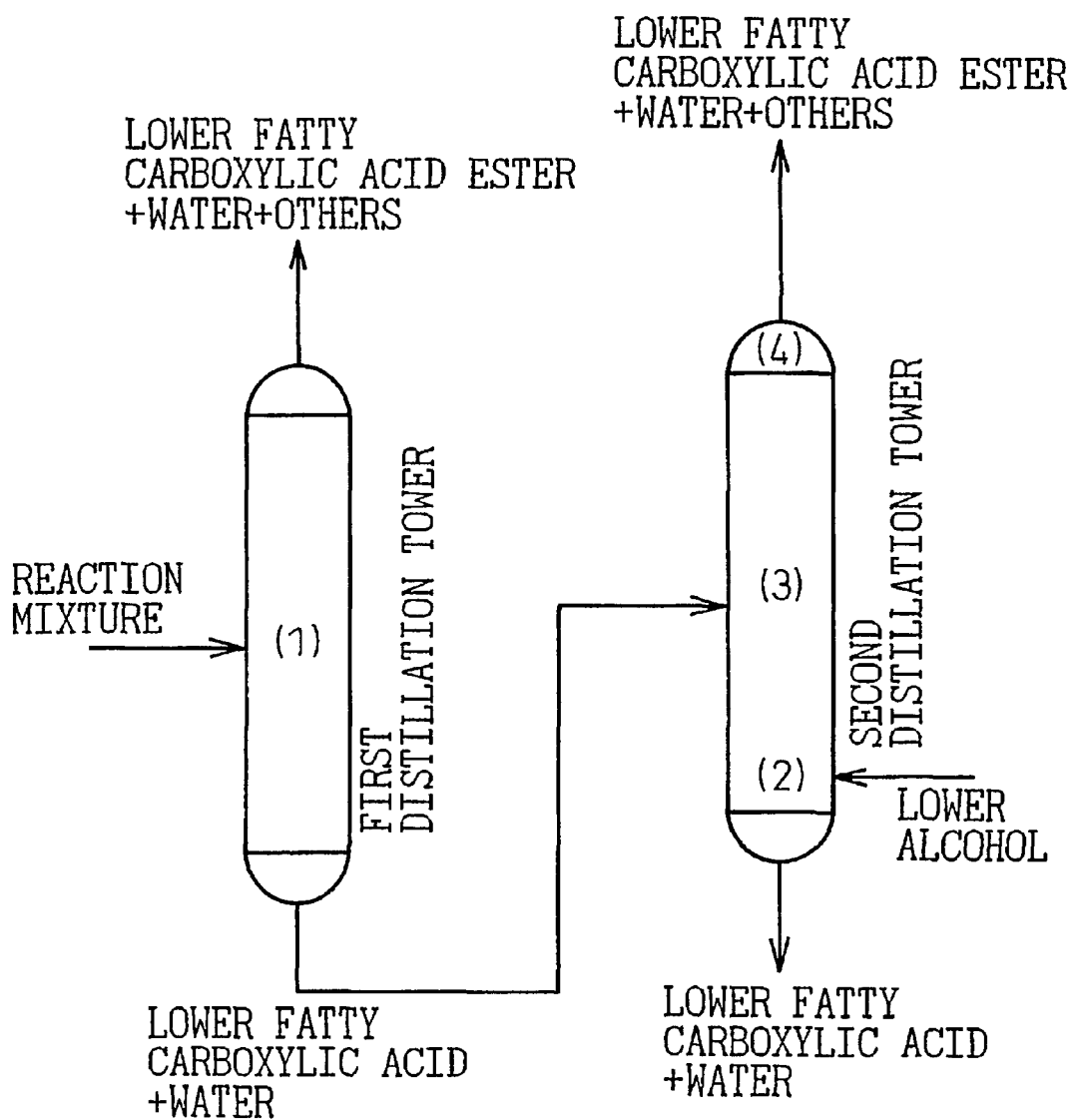
FIG. 2 shows an example of the case where the first step is performed in the first distillation tower and subsequently the second, third and fourth steps are performed in the second distillation tower.
Figure 3:
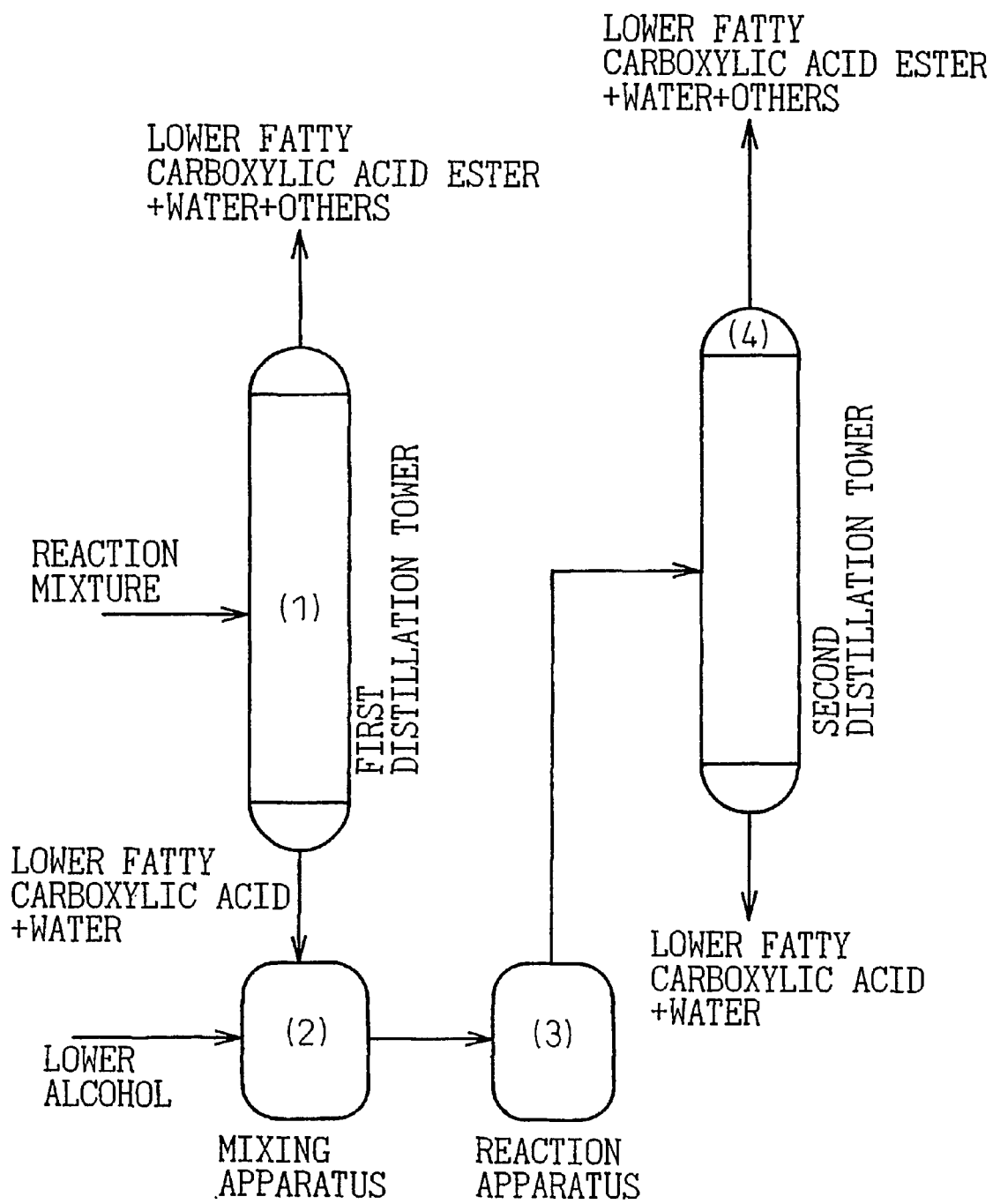
FIG. 3 shows an example of the case where the first step is performed in the first distillation tower, the "moiety substantially containing a lower aliphatic carboxylic acid" obtained from the bottom is introduced into a mixing apparatus, the second step of adding a lower alcohol is performed in the mixing apparatus, the mixture containing the lower aliphatic carboxylic acid and the lower alcohol is then fed to a reaction apparatus, the lower aliphatic carboxylic acid and the lower alcohol are condensed and converted into a lower aliphatic carboxylic acid ester in the reaction apparatus, and the lower aliphatic carboxylic acid ester is finally separated from the mixture in the second distillation tower.

Examples of the embodiment of the present invention (III) include a case where the first to fourth steps all are performed using different apparatuses, a case where all steps are performed using the same apparatus, and a case where a part of these steps are performed using the same apparatus and others are performed using different apparatuses. To speak more specifically, examples thereof include:

1) a case where, as shown in FIG. 1, the first to fourth steps all are performed in one distillation tower;
2) a case where, as shown in FIG. 2, the first step is performed in the first distillation tower and subsequently, the second, third and fourth steps are performed in the second distillation tower; and
3) a case where, as shown in FIG. 3, the first step is performed in the first distillation tower, the "moiety substantially containing a lower aliphatic carboxylic acid as the main component" obtained from the bottom is introduced into a mixing apparatus, the second step of adding a lower alcohol is performed in the mixing apparatus, the mixture containing the lower aliphatic carboxylic acid and the lower alcohol is then fed to a reaction apparatus, the lower aliphatic carboxylic acid and the lower alcohol are condensed and converted into a lower aliphatic carboxylic acid ester in the reaction apparatus, and the lower aliphatic carboxylic acid ester is finally separated from the mixture in the second distillation tower.

The present invention (III) is preferably performed by the method shown in FIG. 1 but this is not particularly limited and the present invention (III) may also be performed by the method shown in FIG. 2 or FIG. 3. Of course, these are not limitative and a combination with other steps, a recycle system not shown or the like may also be used.

The present invention is described in greater detail below by referring to the Examples, however, the present invention should not be construed as being limited thereto.

<Analysis of Solution Collected by Distilling Apparatus>

The analysis was performed using the internal standard method, where an analysis solution was prepared by adding 1 ml of 1,4-dioxane as the internal standard to 10 ml of each solution collected from the top and the bottom and 0.2 $\mu$l of the analysis solution was injected.

Gas Chromatography:
   GC-14B, manufactured by Shimadzu Seisakusho
Column:
   capillary column TC-WAX (length: 30 m, internal diameter: 0.25 mm, film thickness: 25 $\mu$m)
Carrier gas:
   nitrogen (split ratio: 20, column flow rate: 2 ml/min)
Temperature Conditions:
   The detector and the vaporization chamber were constantly at a temperature of 200° C. and the column temperature was kept at 50° C. for 5 minutes from the initiation of analysis, thereafter elevated up to 150° C. at a temperature rising rate of 20° C./min, and kept at 150° C. for 10 minutes.
Detector:
   FID (H$_2$ pressure: 70 kPaG, air pressure: 100 kPaG)

<Preparation of Solution Fed into Distilling Apparatus>

The reaction product, the reaction product having added thereto a lower alcohol, the lower aliphatic carboxylic acid absorber solution, the absorber solution having added thereto a lower alcohol and the lower alcohol were prepared by the following methods.

<Reaction Product>

A reaction product was prepared to the composition shown in Table 1 using the following reagents and pure water.

Acetic acid:
   produced by Wako Pure Chemical Industries, Ltd., special grade reagent, purity: 99.7%
Ethanol:
   produced by Wako Pure Chemical Industries, Ltd., first class reagent, purity: 95%, water: 5%
Ethyl acetate:
   produced by Wako Pure Chemical Industries, Ltd., special grade reagent, purity: 99.5%

<Lower Alcohol>

Using the same ethanol as used in the preparation of the reaction product and pure water, a lower alcohol was prepared to the composition shown in Table 1.

<Reaction Product Having Added Thereto Lower Alcohol>

The reaction product and the lower alcohol each prepared above to the composition shown in Table 1 were mixed at a ratio of 34:4 by mass, whereby a reaction product having added thereto a lower alcohol was prepared to the composition shown in Table 1.

<Lower Aliphatic Carboxylic Acid Absorber Solution>

The reaction product prepared above to the composition shown in Table 1 and acetic acid (produced by Wako Pure Chemical Industries, Ltd., special grade reagent, purity: 99.7%) were mixed at a ratio of 17:10 by mass to prepare a lower aliphatic carboxylic acid absorber solution having the composition shown in Table 1.

<Absorber Solution Having Added Thereto Lower Alcohol>

The lower aliphatic carboxylic acid absorber solution prepared above to the composition shown in Table 1 and a lower ethanol were mixed at a ratio of 34:4 by mass, whereby an absorber solution having added thereto a lower alcohol was prepared to the composition shown in Table 1.

EXAMPLES 1 to 3

The reaction product and the lower alcohol each having the composition shown in Table 1 were fed to an Oldershow distilling apparatus (internal diameter: 27 mm, number of actual plates: 30) and a distillation operation was performed under the conditions shown in Table 2.

The collected solutions sampled from the top and the bottom were analyzed on the components using the above-described analysis method.

The results obtained are shown in Table 3.

TABLE 1

| Feed Solution | Composition [mass %] | | | |
|---|---|---|---|---|
| | Acetic Acid | Ethanol | Ethyl Acetate | Water |
| Reaction product | 39.9 | 0.71 | 35.6 | 23.7 |
| Lower alcohol-added reaction product | 35.7 | 7.8 | 31.9 | 21.2 |
| Lower aliphatic carboxylic acid absorber solution | 62.2 | 0.45 | 22.42 | 14.95 |
| Lower alcohol-added absorber solution | 57.9 | 5.1 | 20.9 | 13.9 |
| Lower alcohol | — | 68.7 | — | 31.3 |

TABLE 2

| | Feed Solution 1 | | | | Feed Solution 2 | | | | Bottom Temperature [° C.] | Operation Pressure [MPaG] | Reflux Ratio [—] |
|---|---|---|---|---|---|---|---|---|---|---|---|
| | Feed Solution | Feed Position [plates] | Feed Amount [parts by mass/h] | Temperature [° C.] | Feed Solution | Feed Position [plates] | Feed Amount [parts by mass/h] | Temperature [° C.] | | | |
| Example 1 | reaction product | 10 | 340 | 60 | lower alcohol | 2 | 40 | 100 | 110 | 0.1 | 1.4 |
| Example 2 | reaction product | 10 | 340 | 60 | lower alcohol | 5 | 40 | 100 | 110 | 0.1 | 1.4 |
| Example 3 | reaction product | 10 | 340 | 60 | lower alcohol | 8 | 40 | 100 | 110 | 0.1 | 1.4 |
| Example 4 | lower alcohol-added reaction product | 10 | 380 | 60 | | | — | | 110 | 0.1 | 1.4 |
| Example 5 | lower aliphatic carboxylic acid absorber solution | 10 | 540 | 60 | lower alcohol | 2 | 40 | 100 | 110 | 0.1 | 1.4 |
| Example 6 | lower alcohol-added absorber solution | 10 | 580 | 60 | | | — | | 110 | 0.1 | 1.4 |
| Comparative Example 1 | reaction product | 10 | 340 | 60 | | | — | | 110 | 0.1 | 1.4 |
| Comparative Example 2 | lower aliphatic carboxylic acid absorber solution | 10 | 540 | 60 | | | — | | 110 | 0.1 | 1.4 |

TABLE 3

| | Top Distillate Product | | | | | Bottom Product | | | | | Recovery of Acetic Acid [%] |
|---|---|---|---|---|---|---|---|---|---|---|---|
| | Outflow [parts by mass/h] | Composition [mass %] | | | | Bottom Amount [parts by mass/h] | Composition [mass %] | | | | |
| | | Acetic Acid | Ethanol | Ethyl Acetate | Water | | Acetic Acid | Ethanol | Ethyl Acetate | Water | |
| Example 1 | 220 | 0.00 | 2.88 | 80.16 | 16.96 | 160 | 64.78 | 6.32 | 0.03 | 28.90 | 21.3 |
| Example 2 | 215 | 0.00 | 3.62 | 77.28 | 19.10 | 165 | 66.74 | 5.44 | 0.03 | 27.82 | 19.9 |

TABLE 3-continued

|  | Top Distillate Product | | | | Bottom Product | | | | | Recovery of Acetic Acid [%] |
|---|---|---|---|---|---|---|---|---|---|---|
|  | Outflow [parts by mass/h] | Composition [mass %] | | | | Bottom Amount [parts by mass/h] | Composition [mass %] | | | |
|  |  | Acetic Acid | Ethanol | Ethyl Acetate | Water |  | Acetic Acid | Ethanol | Ethyl Acetate | Water |  |
| Example 3 | 207 | 0.00 | 3.79 | 74.85 | 21.36 | 173 | 68.45 | 4.11 | 0.01 | 27.44 | 12.8 |
| Example 4 | 201 | 0.00 | 4.02 | 73.96 | 22.02 | 179 | 69.10 | 4.09 | 0.00 | 26.74 | 8.90 |
| Example 5 | 195 | 0.00 | 2.44 | 81.35 | 16.21 | 385 | 75.51 | 2.99 | 0.02 | 21.50 | 33.2 |
| Example 6 | 188 | 0.00 | 2.75 | 78.92 | 18.33 | 392 | 77.38 | 2.35 | 0.00 | 20.27 | 23.9 |
| Comparative Example 1 | 161 | 0.00 | 1.32 | 74.88 | 25.1 | 179 | 76.39 | 0.15 | 0.01 | 23.46 | −0.8 |
| Comparative Example 2 | 158 | 0.00 | 0.88 | 76.63 | 22.49 | 382 | 87.90 | 0.06 | 0.00 | 12.04 | 0.0 |

EXAMPLE 4

A reaction product having added thereto a lower alcohol having the composition shown in Table 1 was fed to an Oldershow distilling apparatus (internal diameter: 27 mm, number of actual plates: 30) and a distillation operation was performed under the conditions shown in Table 2.

The collected solutions sampled from the top and the bottom were analyzed on the components using the above-described analysis method.

The results obtained are shown in Table 3.

EXAMPLE 5

A lower aliphatic carboxylic acid absorber solution and the lower alcohol the lower alcohol each having the composition shown in Table 1 were fed to an Oldershow distilling apparatus (internal diameter: 27 mm, number of actual plates: 30) and a distillation operation was performed under the conditions shown in Table 2.

The collected solutions sampled from the top and the bottom were analyzed on the components using the above-described analysis method.

The results obtained are shown in Table 3.

EXAMPLE 6

An absorber solution having added thereto a lower alcohol having the composition shown in Table 1 was fed to an Oldershow distilling apparatus (internal diameter: 27 mm, number of actual plates: 30) and a distillation operation was performed under the conditions shown in Table 2.

The collected solutions sampled from the top and the bottom were analyzed on the components using the above-described analysis method.

The results obtained are shown in Table 3.

COMPARATIVE EXAMPLE 1

A reaction solution having the composition shown in Table 1 was fed to an Oldershow distilling apparatus (internal diameter: 27 mm, number of actual plates: 30) and a distillation operation was performed under the conditions shown in Table 2.

The collected solutions sampled from the top and the bottom were analyzed on the components using the above-described analysis method.

The results obtained are shown in Table 3.

COMPARATIVE EXAMPLE 2

A lower aliphatic carboxylic acid absorber solution having the composition shown in Table 1 was fed to an Oldershow distilling apparatus (internal diameter: 27 mm, number of actual plates: 30) and a distillation operation was performed under the conditions shown in Table 2.

The collected solutions sampled from the top and the bottom were analyzed on the components using the above-described analysis method.

The results obtained are shown in Table 3.

Industrial Applicability

It is apparent from the results in the foregoing pages that in the process for producing a lower aliphatic carboxylic acid ester by a gas phase esterification reaction starting from a lower aliphatic carboxylic acid and a lower olefin, when a step of adding a lower alcohol corresponding to a hydrate of the lower olefin to the reaction product containing a lower aliphatic carboxylic acid after the gas phase reaction, condensing the alcohol and the lower aliphatic carboxylic acid and while allowing the conversion into a lower aliphatic carboxylic acid ester to proceed, separating the lower aliphatic carboxylic acid ester is added, the conversion of a lower aliphatic carboxylic acid into a lower aliphatic carboxylic acid ester, which has been difficult to attain only by the method of using excess lower olefin to the lower aliphatic carboxylic acid in a gas phase reaction, can be improved and in turn, a lower aliphatic carboxylic acid ester can be efficiently produced.

Furthermore, it is also apparent that the above-described step can be performed in a distillation tower as an existing apparatus for separating a lower aliphatic carboxylic acid ester from the gas phase reaction product and therefore, complicated modification of production equipment is not necessary.

What is claimed is:

1. A process for producing lower aliphatic carboxylic acid ester, comprising reacting a lower aliphatic carboxylic acid and a lower olefin in a gas phase in the presence of an acid catalyst, wherein the production process comprises the following first and second steps:

First step:
   a step of separately feeding a lower alcohol corresponding to a hydrate of the lower olefin to the reaction product containing a lower aliphatic carboxylic acid after the gas phase reaction and thereby obtaining a reaction product having added thereto a lower alcohol; and Second step:
a step of condensing the lower aliphatic carboxylic acid and the lower alcohol in the reaction product having added thereto a lower alcohol, obtained in the first step, and while allowing the conversion into a lower aliphatic carboxylic acid ester to proceed, separating the lower carboxylic acid ester.

2. A process as claimed in claim 1, wherein the first step and the second step are performed in the same apparatus.

3. A process as claimed in claim 1, wherein the apparatus for performing the second step is a distilling apparatus.

4. A process for producing a lower aliphatic carboxylic acid ester, comprising reacting a lower aliphatic carboxylic acid and a lower olefin in a gas phase in the presence of an acid catalyst, wherein the production process comprises the following first to third steps:

First step:
a step of adding the same lower aliphatic carboxylic acid as used in the reaction to the reaction product containing a lower aliphatic carboxylic acid after the gas phase reaction and thereby obtaining a reaction product having added thereto a lower aliphatic carboxylic acid:

Second step:
a step of separately feeding a lower alcohol corresponding to a hydrate of the lower olefin to the reaction product having added thereto a lower aliphatic carboxylic acid, obtained in the first step, and thereby obtaining a reaction product having added thereto a lower alcohol; and Third step:
a step of condensing the lower aliphatic carboxylic acid and the lower alcohol in the reaction product having added thereto a lower alcohol, obtained in the second step, and while allowing the conversion into a lower aliphatic carboxylic acid ester, separating the lower aliphatic carboxylic acid ester.

5. A process as claimed in claim 4, wherein the first to third steps are performed in the same apparatus.

6. A process as claimed in claim 4, wherein the apparatus for performing the third step is a distilling apparatus.

7. A process for producing a lower aliphatic carboxylic acid ester, comprising reacting a lower aliphatic carboxylic acid and a lower olefin in a gas phase in the presence of an acid catalyst, wherein the production process comprises the following first to fourth steps;

First step:
a step of separating the reaction product after the gas phase reaction containing a lower aliphatic carboxylic acid and a lower aliphatic carboxylic acid ester into a moiety substantially containing a lower aliphatic carboxylic acid as the main component and a moiety substantially containing a lower aliphatic carboxylic acid ester as the main component;

Second step:
a step of adding a lower alcohol corresponding to a hydrate of the lower olefin to the moiety substantially containing a lower aliphatic carboxylic acid as the main component, obtained in the first step, and thereby obtaining a product having added thereto a lower alcohol;

Third step:
a step of condensing the lower aliphatic carboxylic acid and the lower alcohol contained in the product having added thereto a lower alcohol, obtained in the second step, to cause conversion into a lower aliphatic carboxylic acid ester; and Fourth step:
a step of separating the lower aliphatic carboxylic acid ester obtained in the third step and thereby obtaining a lower aliphatic carboxylic acid ester.

8. A process as claimed in claim 7, wherein the first step is performed in a distilling apparatus.

9. A process as claimed in claim 7, wherein the first step is performed in a distilling apparatus, and the second step is performed in the same distilling apparatus as used in the first step.

10. A process as claimed in claim 9, wherein the position of feeding a lower alcohol to the distilling apparatus is lower than the position of feeding the reaction product after the gas phase reaction containing a lower aliphatic carboxylic acid and a lower aliphatic carboxylic acid ester to the distilling apparatus.

11. A process as claimed in any one of claims 7 to 10, wherein the third step is performed in the same apparatus as used in the first step and/or the second step.

12. A process as claimed in any one of claims 7 to 10, wherein the fourth step is performed in the same apparatus as in the first step, the second step and/or the third step.

13. A process as claimed claim 7, wherein the acid catalyst is obtained by mounting at least one member selected from the group consisting of heteropolyacids and heteropolyacid salts on a support.

14. A process as claimed claim 7, wherein a part or all of the lower alcohol described in the second step of claim 7 is a lower alcohol produced as a by-product when a lower aliphatic carboxylic acid and a lower olefin are reacted in a gas phase in the presence of an acid catalyst.

15. A process as claimed claim 7, wherein the amount added of the lower alcohol described in the second step of claim 7 is, in terms of the molar ratio to the lower aliphatic carboxylic acid in the reaction solution before the addition of the alcohol, from 1:1 to 1:15 (lower alcohol: lower aliphatic carboxylic acid).

16. A process as claimed claim 7, wherein the lower olefin is at least one member selected from the group consisting of ethylene, propylene, 1-butene, 2-butene and 1-pentene.

17. A process as claimed claim 7, wherein the lower aliphatic carboxylic acid is at least one member selected from the group consisting of formic acid, acetic acid, propionic acid, acrylic acid and butyric acid.

18. A process as claimed in claim 7, wherein the lower olefin is ethylene and the lower aliphatic carboxylic acid is acetic acid.

19. A process as claimed in claim 2, wherein the apparatus for performing the second step is a distilling apparatus.

20. A process as claimed in claim 5, wherein the apparatus for performing the third step is a distilling apparatus.

21. A process as claimed in any one of claims 1 and 4, wherein the acid catalyst is obtained by mounting at least one member selected from the group consisting of heteropolyacids and heteropolyacid salts on a support.

22. A process as claimed in any one of claim 1 or 4, wherein a part or all of the lower alcohol described in the first step of claim 1 or the second step of claim 4 is a lower alcohol produced as a by-product when a lower aliphatic carboxylic acid and a lower olefin are reacted in a gas phase in the presence of an acid catalyst; and
the lower alcohol produced as a by-product is obtained through separation and recovery.

23. A process as claimed in any one of claim 1 or 4, wherein the amount added of the lower alcohol described in the first step of claim 1 or the second step of claim 4 is, in terms of the molar ratio to the lower aliphatic carboxylic acid in the reaction solution before the addition of the alcohol, from 1:1 to 1:15 (lower alcohol: lower aliphatic carboxylic acid).

24. A process as claimed in any one of claim 1 or 4, wherein the lower olefin is at least one member selected from the group consisting of ethylene, propylene, 1-butene, 2-butene and 1-pentene.

25. A process as claimed in any one of claim 1 or 4, wherein the lower aliphatic carboxylic acid is at least one member selected from the group consisting of formic acid, acetic acid, propionic acid, acrylic acid and butyric acid.

26. A process as claimed in any one of claim 1 or 4, wherein the lower olefin is ethylene and the lower aliphatic carboxylic acid is acetic acid.

\* \* \* \* \*